# (12) United States Patent
Honda et al.

(10) Patent No.: US 9,888,959 B2
(45) Date of Patent: Feb. 13, 2018

(54) THERAPEUTIC TREATMENT SYSTEM AND OPERATION METHOD FOR THERAPEUTIC TREATMENT SYSTEM

(71) Applicant: OLYMPUS CORPORATION, Hachioji-shi, Tokyo (JP)

(72) Inventors: Yoshitaka Honda, Hachioji (JP); Tsuyoshi Hayashida, Hachioji (JP); Kazue Tanaka, Sagamihara (JP); Sumihito Konishi, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/203,361

(22) Filed: Jul. 6, 2016

(65) Prior Publication Data

US 2016/0310207 A1 Oct. 27, 2016

Related U.S. Application Data

(63) Continuation of application No. PCT/JP2015/072047, filed on Aug. 4, 2015.

(30) Foreign Application Priority Data

Aug. 5, 2014 (JP) ................................. 2014-159774

(51) Int. Cl.
*A61B 18/14* (2006.01)
*A61B 18/08* (2006.01)
(Continued)

(52) U.S. Cl.
CPC ........ *A61B 18/1445* (2013.01); *A61B 18/085* (2013.01); *A61B 2017/00115* (2013.01);
(Continued)

(58) Field of Classification Search
CPC ........... A61B 2018/00916; A61B 2018/00922; A61B 18/1442; A61B 18/1445; A61B 18/085
See application file for complete search history.

(56) References Cited

U.S. PATENT DOCUMENTS 6,306,131 B1 10/2001 Hareyama et al.
2003/0073987 A1 4/2003 Sakurai et al.
(Continued)

FOREIGN PATENT DOCUMENTS

EP 1 878 399 A1 1/2008
EP 1 878 400 A1 1/2008
(Continued)

OTHER PUBLICATIONS

Nov. 10, 2015 Search Report issued in International Patent Application No. PCT/JP2015/072047.
(Continued)

*Primary Examiner* — Ronald Hupczey, Jr.
*Assistant Examiner* — Bo Ouyang
(74) *Attorney, Agent, or Firm* — Oliff PLC

(57) ABSTRACT

A therapeutic treatment system includes a holding section configured to hold a biological tissue, electrodes provided in the holding section and capable of outputting first high-frequency energy for sealing the biological tissue at a first sealing temperature and second high-frequency energy for dissecting the biological tissue at a first dissection temperature higher than the first sealing temperature, electrodes provided in the holding section and capable of outputting first thermal energy for sealing the biological tissue at a second sealing temperature higher than the first sealing temperature and second thermal energy for dissecting the biological tissue at a second dissection temperature lower than the first dissection temperature and higher than the second sealing temperature, and a control section configured (Continued)

to control temperature of each of the electrodes to output the second thermal energy after the output of the first high-frequency energy.

15 Claims, 10 Drawing Sheets

(51) Int. Cl.
*A61B 17/00* (2006.01)
*A61B 18/00* (2006.01)

(52) U.S. Cl.
CPC .............. *A61B 2017/00199* (2013.01); *A61B 2017/00973* (2013.01); *A61B 2018/0063* (2013.01); *A61B 2018/00601* (2013.01); *A61B 2018/00607* (2013.01); *A61B 2018/00654* (2013.01); *A61B 2018/00714* (2013.01); *A61B 2018/00791* (2013.01); *A61B 2018/00875* (2013.01)

(56) References Cited

U.S. PATENT DOCUMENTS

| | | |
|---|---|---|
| 2003/0171747 A1 | 9/2003 | Kanehira et al. |
| 2006/0084973 A1* | 4/2006 | Hushka .............. A61B 18/1445 606/42 |
| 2006/0217697 A1* | 9/2006 | Lau .................. A61B 17/29 606/29 |
| 2008/0015567 A1 | 1/2008 | Kimura |
| 2008/0015575 A1 | 1/2008 | Odom et al. |
| 2008/0195093 A1 | 8/2008 | Couture et al. |
| 2009/0248002 A1 | 10/2009 | Takashino et al. |
| 2010/0268205 A1* | 10/2010 | Manwaring .......... A61B 18/082 606/29 |
| 2011/0288369 A1* | 11/2011 | Ginnebaugh ........ A61B 18/085 600/36 |
| 2012/0022517 A1* | 1/2012 | Stuebe ................ A61B 18/085 606/31 |
| 2012/0059371 A1* | 3/2012 | Anderson .......... A61B 18/1445 606/45 |
| 2013/0150848 A1* | 6/2013 | Yasunaga ............. A61B 18/085 606/41 |

FOREIGN PATENT DOCUMENTS

| | | |
|---|---|---|
| EP | 1 958 583 A2 | 8/2008 |
| JP | 2000-107197 A | 4/2000 |
| JP | 2003-116871 A | 4/2003 |
| JP | 2005-058405 A | 3/2005 |
| JP | 2008-018226 A | 1/2008 |
| JP | 2008-023335 A | 2/2008 |
| JP | 2008-212663 A | 9/2008 |
| JP | 2012-161566 A | 8/2012 |
| JP | 2012-254324 A | 12/2012 |

OTHER PUBLICATIONS

Mar. 29, 2016 Decision to Grant a Patent issued in Japanese Patent Application No. 2016-506708.
Aug. 31, 2017 Extended European Search Report in European Patent Application No. 15830568.0.

* cited by examiner

THERAPEUTIC TREATMENT SYSTEM AND OPERATION METHOD FOR THERAPEUTIC TREATMENT SYSTEM

CROSS REFERENCE TO RELATED APPLICATION

This application is a continuation application of PCT/JP2015/072047 filed on Aug. 4, 2015 and claims benefit of Japanese Application No. 2014-159774 filed in Japan on Aug. 5, 2014, the entire contents of which are incorporated herein by this reference.

BACKGROUND OF INVENTION

1. Field of the Invention

The present invention relates to a therapeutic treatment system and an operation method for the therapeutic treatment system and, more particularly, to a therapeutic treatment system and an operation method for the therapeutic treatment system capable of outputting two energy outputs of high-frequency energy and thermal energy.

2. Description of the Related Art

There has been known a therapeutic treatment apparatus for treating a biological tissue using high-frequency energy or thermal energy. For example, Japanese Patent Application Laid-Open Publication No. 2012-161566 proposes a therapeutic treatment apparatus including a holding section that holds a biological tissue, which is a treatment target, and including a high-frequency electrode for applying a high-frequency voltage to a portion where the holding section and the biological tissue are in contact and a heater for heating the high-frequency electrode.

Treatment for sealing or dissecting a biological tissue such as a blood vessel or a bile duct with high-frequency energy or treatment for sealing or dissecting the biological tissue with thermal energy has been performed using such a therapeutic treatment apparatus.

Japanese Patent Application Laid-Open Publication No. 2012-254324 proposes a treatment instrument for effectively performing sealing by preheating an electrode that outputs a high-frequency current.

SUMMARY OF THE INVENTION

A therapeutic treatment system according to an aspect of the present invention includes: a pair of holding members for holding a biological tissue, which is a treatment target, such that at least one of the holding members moves to open and close relatively to another; a high-frequency-energy output section provided in at least one of the holding members and capable of outputting first high-frequency energy for sealing the biological tissue by setting the biological tissue to a first sealing temperature and second high-frequency energy for dissecting the biological tissue at a first dissection temperature higher than the first sealing temperature; a thermal-energy output section provided in at least one of the holding members and capable of outputting first thermal energy for sealing the biological tissue by setting the biological tissue to a second sealing temperature higher than the first sealing temperature and second thermal energy for dissecting the biological tissue at a second dissection temperature lower than the first dissection temperature and higher than the second sealing temperature; and a control section configured to control respective temperatures of the high-frequency-energy output section and the thermal-energy output section to output the second thermal energy by the thermal-energy output section after the output of the first high-frequency energy by the high-frequency-energy output section.

An operation method for a therapeutic treatment system according to an aspect of the present invention is an operation method for a therapeutic treatment system including a pair of holding members for holding a biological tissue, which is a treatment target, such that at least one of the holding members moves to open and close relatively to another, a high-frequency-energy output section provided in at least one of the grasping members and capable of outputting first high-frequency energy for sealing the biological tissue by setting the biological tissue to a first sealing temperature and second high-frequency energy for dissecting the biological tissue at a first dissection temperature higher than the first sealing temperature; a thermal-energy output section provided in at least one of the holding members and capable of outputting first thermal energy for sealing the biological tissue by setting the biological tissue to a second sealing temperature higher than the first sealing temperature and second thermal energy for dissecting the biological tissue at a second dissection temperature lower than the first dissection temperature and higher than the second sealing temperature; and a control section, wherein the control section controls the high-frequency-energy output section and the thermal-energy output section to output the second thermal energy by the thermal-energy output section after the output of the first high-frequency energy by the high-frequency-energy output section.

DETAILED DESCRIPTION OF THE PREFERRED EMBODIMENTS

An embodiment of the present invention is explained below with reference to the drawings.

(Overall Configuration)

Figure 1:
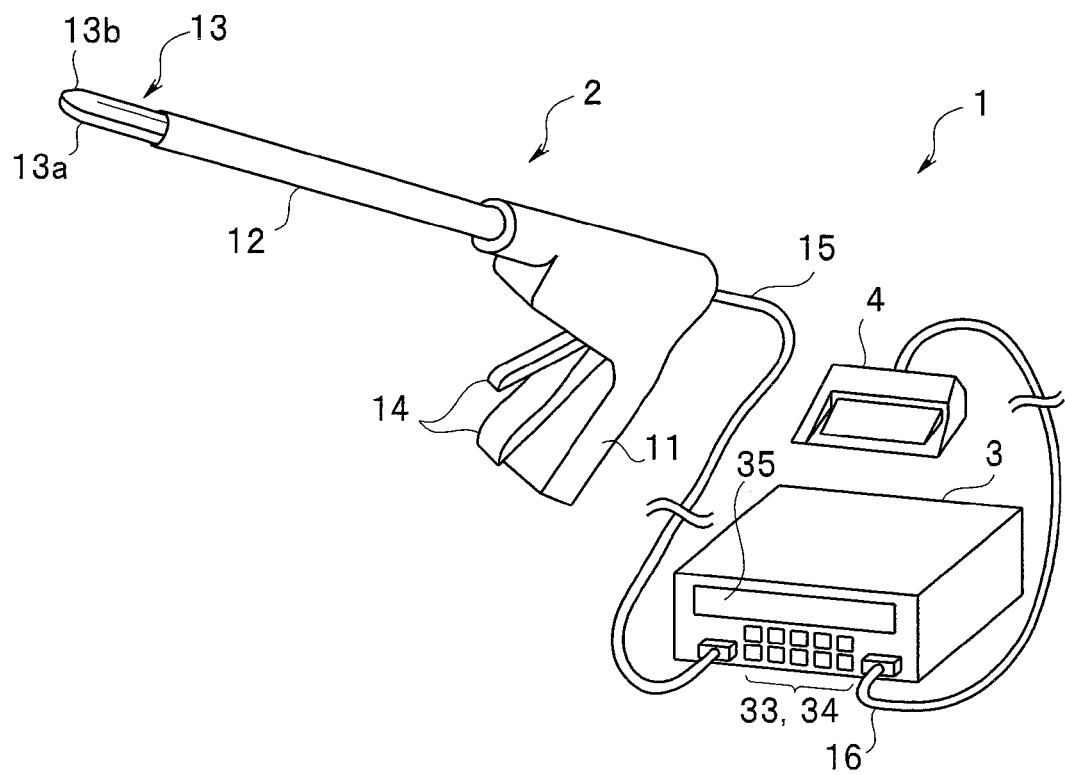
FIG. 1 is a configuration diagram showing a configuration of a therapeutic treatment system 1 according to an embodiment of the present invention.

FIG. 1 is a configuration diagram showing a configuration of a therapeutic treatment system 1 according to the present embodiment.

The therapeutic treatment system 1 according to the present embodiment is a system used in treatment of a biological tissue and capable of causing high-frequency energy and thermal energy to act on the biological tissue.

As shown in FIG. 1, the therapeutic treatment system 1 includes a treatment instrument 2, a main body apparatus 3 including energy sources for high-frequency energy and thermal energy, and a footswitch 4.

The treatment instrument 2 is a treatment instrument for surgical treatment to be pierced through, for example, an abdominal wall to perform treatment. The treatment instrument 2 includes a handle 11, a shaft 12 attached to the handle 11, and a holding section 13 provided at a distal end of the shaft 12. The holding section 13 includes two jaw members 13a and 13b capable of opening and closing. The holding section 13 is a treatment section that holds a biological tissue serving as a treatment target and performs treatment such as coagulation and dissection. In the following explanation, the holding section 13 side is referred to as distal end side and the handle 11 side is referred to as proximal end side. The handle 11 includes a plurality of operation levers 14 for operating opening and closing of the holding section 13.

Note that, naturally, a shape of the treatment instrument 2 described here is an example. The treatment instrument 2 may have another shape as long as the treatment instrument 2 has the same functions. For example, the other shape of the treatment instrument 2 may be of a type in which the holding section 13 (the jaw members 13a and 13b) bends in a predetermined direction or a type in which the shaft 12 bends in a predetermined direction.

The treatment instrument 2 is connected to the main body apparatus 3 functioning as a power supply apparatus via a cable 15 extending from the handle 11. The footswitch 4 is connected to the main body apparatus 3 via a cable 16. A surgeon operates a pedal of the footswitch 4, whereby ON and OFF of supply of energy from the main body apparatus 3 to the treatment instrument 2 are switched. Note that, although the footswitch 4 is used, the footswitch 4 operated by a foot may be replaced with a switch operated by a hand or other switches.

(Configuration of the Holding Section)

Figure 2:
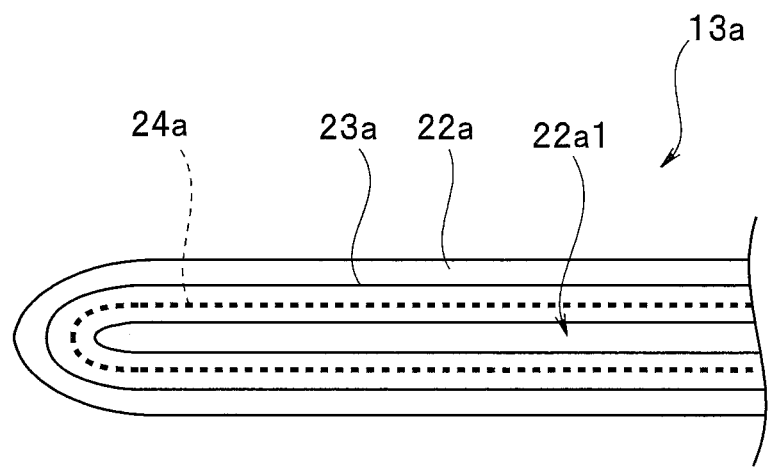
FIG. 2 is a partial plan view of a holding surface of a jaw member 13*a* on a lower side of two jaw members of a holding section 13 according to the embodiment of the present invention.
Figure 3:
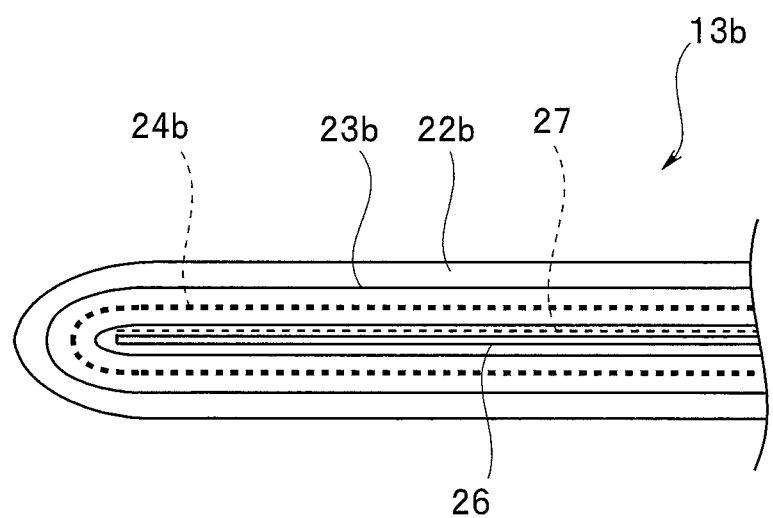
FIG. 3 is a partial plan view of a holding surface of a jaw member 13*b* on an upper side of the two jaw members of the holding section 13 according to the embodiment of the present invention.
Figure 4:
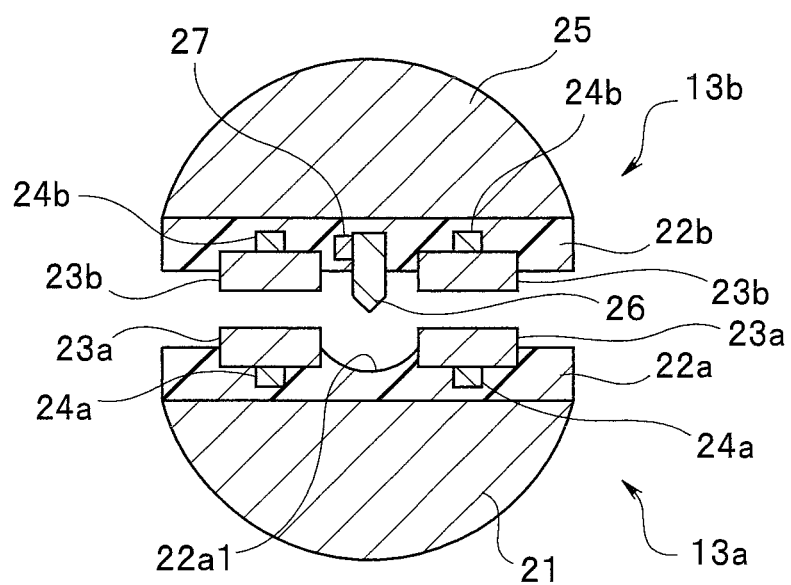
FIG. 4 is a sectional perspective view of the holding section 13 orthogonal to an axial direction of a shaft 12 according to the embodiment of the present invention.

FIG. 2 to FIG. 4 are diagrams for explaining a configuration of the holding section 13. FIG. 2 is a partial plan view of a holding surface of the jaw member 13a on a lower side of the two jaw members of the holding section 13. FIG. 3 is a partial plan view of a holding surface of the jaw member 13b on an upper side of the two jaw members of the holding section 13. FIG. 4 is a sectional perspective view of the holding section 13 orthogonal to an axial direction of the shaft 12.

The jaw member 13a includes a jaw main body section 21. On the holding surface side of the jaw main body section 21, an insulating section 22a made of an insulating material is provided and a U-shaped electrode 23a is provided to project from a surface of the insulating section 22a. A U-shaped heater 24a is provided to be closely attached to a rear side of the electrode 23a. On a front surface of the insulating section 22a, a linear groove 22a1, which receives a dissection electrode 26 (FIG. 3) provided in the jaw member 13b, is formed.

The jaw member 13b includes a jaw main body section 25. On the holding surface side of the jaw main body section 25, an insulating section 22b made of an insulating material is provided and a U-shaped electrode 23b and a linear dissection electrode 26 are provided to project from a front surface of the insulating section 22b. A U-shaped heater 24b is provided to be closely attached to a rear surface of the electrode 23b.

The linear electrode 26 is an electrode for dissection. A high-frequency current is supplied to the electrode 26 when dissection treatment is performed. A heater 27 is provided to be closely attached to the electrode 26.

Note that the electrodes 23a and 23b and the heaters 24a and 24b respectively provided in the jaw members 13a and 13b are not limited to the shapes shown in FIG. 2 and FIG. 3. For example, a linear electrode and a linear heater closely attached to the electrode may be provided in the jaw member 13a. A plurality of electrodes and a plurality of heaters closely attached to the electrodes may be provided in the jaw member 13a. The same applies to the jaw member 13b.

The jaw members 13a and 13b are a pair of holding members that holds a biological tissue, which is a treatment target. That is, the jaw members 13a and 13b are a pair of holding members including holding surfaces opposed to each other for holding the biological tissue, which is the treatment target, such that at least one of the holding members moves to open and close relatively to the other.

The electrodes 23a, 23b, and 26 are high-frequency-energy output sections and connected to the main body apparatus 3 by a not-shown signal line. The heaters 24a, 24b, and 27 are thermal-energy output sections and connected to the main body apparatus 3 by a not-shown signal line. Heat generated in the heaters 24a, 24b, and 27 is transmitted to the biological tissue respectively via the electrodes 23a, 23b, and 26.

Sealing treatment for the biological tissue by high-frequency energy is performed by allowing a predetermined high-frequency current to flow between the electrode 23a and the electrode 23b in a state in which the biological tissue is held between the electrode 23a and the electrode 23b.

Dissection treatment for the biological tissue by high-frequency energy is performed by allowing a high-frequency current having a voltage higher than a voltage of the electric current during the sealing to flow between the electrode 23a or 23b and the electrode 26 in a state in which the biological tissue is held between the electrode 23a and the electrode 23b.

Sealing treatment for the biological tissue by thermal energy is performed by setting the heaters 24a and 24b to a predetermined temperature in the state in which the biological tissue is held between the electrodes 23a and 23b.

Dissection treatment for the biological tissue by thermal energy is performed by setting the heater 27 to temperature higher than the temperature during the sealing in the state in which the biological tissue is held between the electrodes 23a and 23b.

Figure 5:
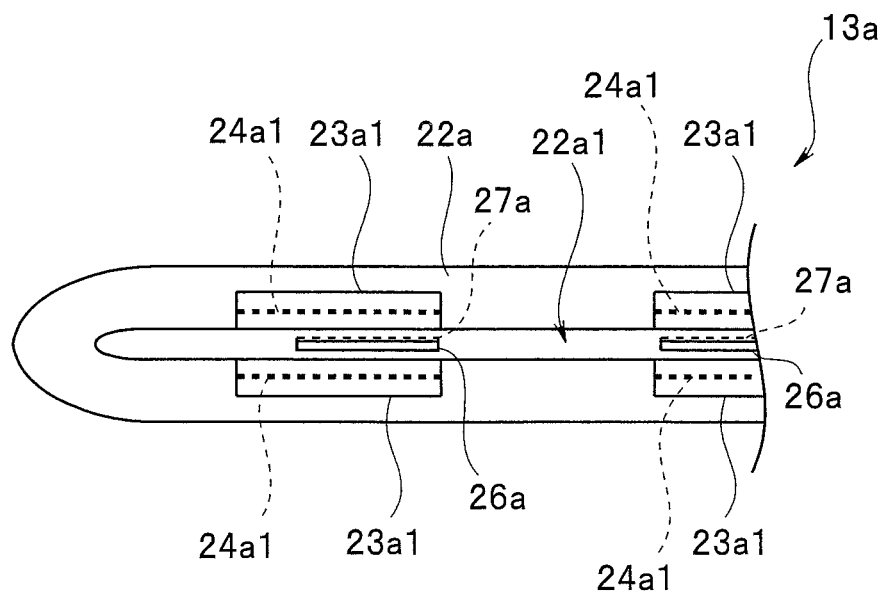
FIG. 5 is a partial plan view of the holding surface of the jaw member 13*a* on the lower side of the two jaw members of the holding section 13 showing another shape example of electrodes and heaters according to the embodiment of the present invention.
Figure 6:
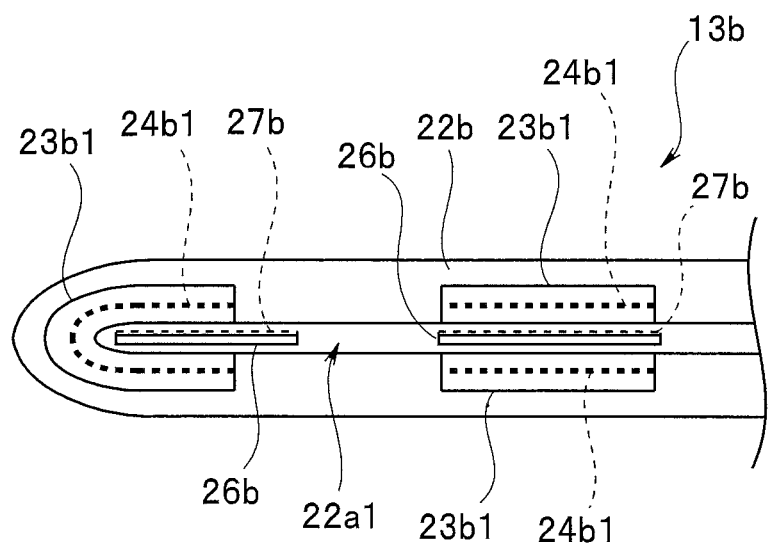
FIG. 6 is a partial plan view of the holding surface of the jaw member 13*b* on the upper side of the two jaw members of the holding section 13 showing another shape example of the electrodes and the heaters according to the embodiment of the present invention.

Note that shapes of the electrodes and the heaters provided in the holding section 13 may be shapes other than the shapes shown in FIG. 2 to FIG. 4. FIG. 5 and FIG. 6 are diagrams showing other shape examples of the electrodes and the heaters provided in the holding section 13. FIG. 5 is a partial plan view of the holding surface of the jaw member 13a on the lower side of the two jaw members of the holding section 13 showing another shape example of the electrodes and the heaters. FIG. 6 is a partial plan view of the holding surface of the jaw member 13b on the upper side of the two jaw members of the holding section 13 showing another shape example of the electrodes and the heaters.

A plurality of electrodes 23a1 are disposed on the holding surface of the jaw member 13a on the lower side. Heaters 24a1 are provided to be closely attached to rear surfaces of the respective electrodes 23a1. Further, a plurality of electrodes 26a, which are dissection electrodes, are disposed in the linear groove 22a1 on the holding surface of the jaw member 13b on the lower side. Heaters 27a are provided to be closely attached to the respective electrodes 26a.

A plurality of electrodes 23b1 are disposed on the holding surface of the jaw member 13b on the upper side. Heaters 24b1 are provided to be closely attached to rear surfaces of the respective electrodes 23b1. Further, a plurality of electrodes 26b, which are dissection electrodes, are disposed in the linear groove 22a1 on the holding surface of the jaw member 13b on the upper side. Heaters 27b are provided to be closely attached to the respective electrodes 26a.

The respective electrodes 23a1 and 23b1 are alternately disposed not to come into contact with each other when the two jaw members 13a and 13b are closed. Similarly, the respective electrodes 26a and 26b are alternately disposed not to come into contact with each other when the two jaw members 13a and 13b are closed.

Note that, in the case of FIG. 5 and FIG. 6, each of the plurality of electrodes 23a1, 23b1, 26a, and 26b and each of the plurality of heaters 24a1, 24b1, 27a, and 27b may be enabled to individually operate to change output states of high-frequency energy and thermal energy on a distal end side, a center portion, and a proximal end side of the holding section 13.

(Configuration of the Main Body Apparatus)

Figure 7:
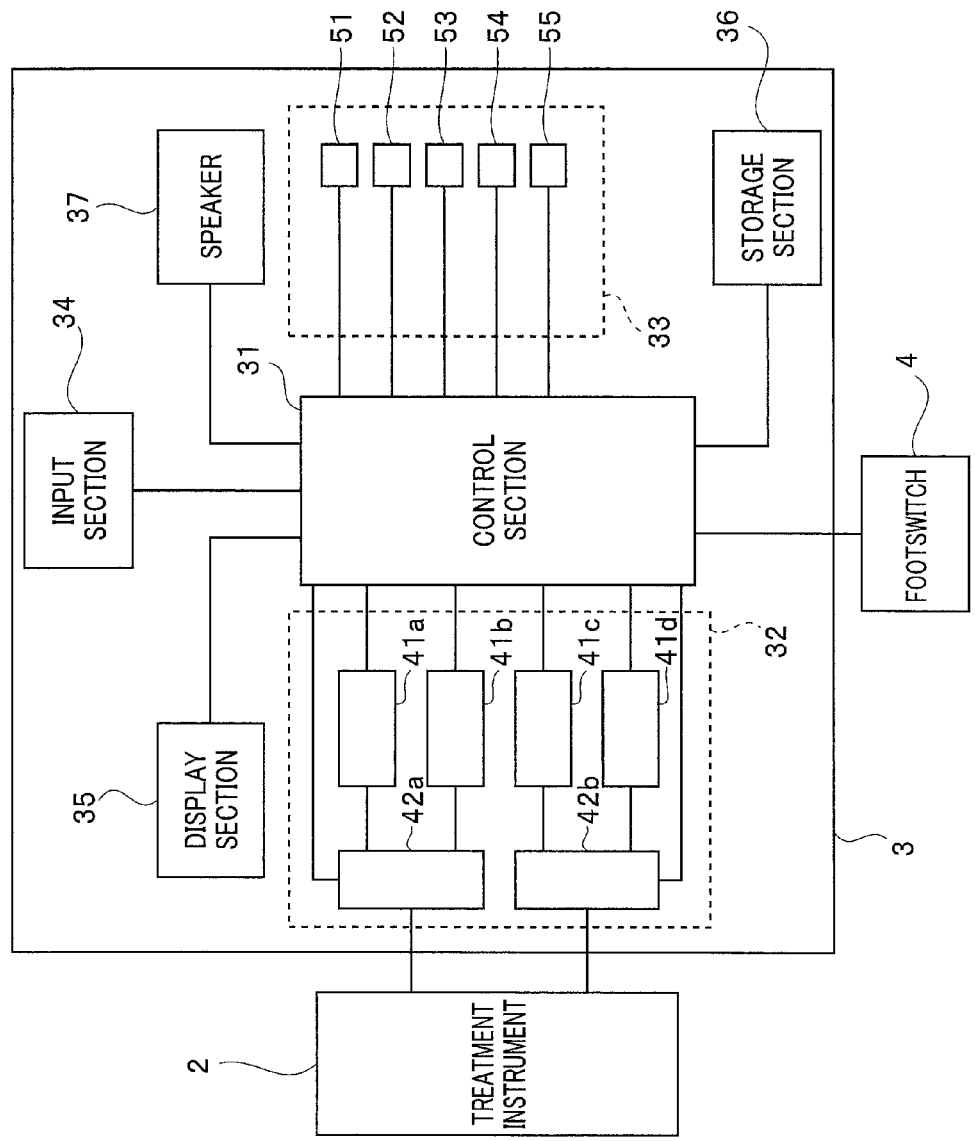
FIG. 7 is a block diagram showing a configuration of a main body apparatus 3 according to the embodiment of the present invention.

FIG. 7 is a block diagram showing a configuration of the main body apparatus 3. The main body apparatus 3 is a therapeutic treatment apparatus including a control section 31, an energy output section 32, an output-sequence setting section 33, an input section 34, a display section 35, a storage section 36, and a speaker 37.

The control section 31 includes a central processing unit (CPU), a ROM, and a RAM and controls the entire main body apparatus 3. The control section 31 controls the energy output section 32 such that an energy output is performed from the treatment instrument 2 to a biological tissue in an output sequence set in the output-sequence setting section 33.

The energy output section 32 is an output circuit for giving high-frequency energy and thermal energy to the biological tissue. The energy output section 32 includes a high-frequency output circuit 41a that outputs a high-frequency current for sealing treatment to the electrodes 23a and 23b, a high-frequency output circuit 41b that outputs a high-frequency current for dissection treatment to the electrodes 23a (or 23b) and 26, a heater driving circuit 41c that outputs a driving current for heating the heaters 24a and 24b to temperature for sealing treatment, a heater driving circuit 41d that outputs a driving current for heating the heater 27 to temperature for dissection treatment, a detection circuit 42a for detecting impedance Z between the electrodes 23a and 23b or between the electrodes 23a (or 23b) and 26 during a high-frequency output, and a detection circuit 42b for detecting resistance R of the respective heaters 24a and 24b or resistance R of the heater 27 during heater driving. Note that, in the present embodiment, since the respective heaters 24a, 24b, and 27 generate heat with a DC driving current, the detection circuit 42b detects the resistance R of the respective heaters 24a, 24b, and 27. On the other hand, when the respective heaters 24a, 24b, and 27 generate heat with an AC driving current, the detection circuit 42b detects impedance of the respective heaters 24a, 24b, and 27. The high-frequency output circuits 41a and 41b and the heater driving circuits 41c and 41d are driven under the control by the control section 31.

The high-frequency output circuit 41a is a circuit that outputs a high-frequency current for sealing the biological tissue. The high-frequency output circuit 41a outputs a high-frequency current of a sine wave of 200 KHz to 500 KHz to the electrodes 23a and 23b of the treatment instrument 2 to fuse the biological tissue at temperature between 60° C. and 100° C. In an example explained below, the high-frequency output circuit 41a sets the biological tissue to temperature of 100° C.

The high-frequency output circuit 41a supplies a high-frequency current to flow between the electrodes 23a and 23b. The biological tissue is fused by Joule heat due to the high-frequency current while the impedance Z between the electrodes 23a and 23b detected by the detection circuit 42a is monitored by the control section 31.

The high-frequency output circuit 41a is a circuit driven during a mode M1. The mode M1 is a mode in which fast sealing treatment is possible because the Joule heat is used.

The high-frequency output circuit 41b is a circuit that outputs a high-frequency current for dissecting the biological tissue. In order to dissect the biological tissue at temperature between 200° C. and 400° C., the high-frequency output circuit 41b outputs a discontinuous high-frequency current of a sine wave of 200 KHz to 500 KHz to the treatment instrument 2 at voltage higher than the voltage during the sealing. In an example explained below, the high-frequency output circuit 41b sets the biological tissue to temperature between 300° C. and 400° C.

The high-frequency output circuit 41b supplies the high-frequency current to flow between the electrode 23a (or 23b) and the electrode 26. The biological tissue is vaporized and dissected by heat due to radiation of the high-frequency current while the impedance Z between the electrode 23a (or 23b) and the electrode 26 detected by the detection circuit 42a is monitored by the control section 31.

The high-frequency output circuit 41b is a circuit driven during a mode M2.

Note that the high-frequency output circuits 41a and 41b are individual circuits. However, the high-frequency output circuits 41a and 41b may be realized by one circuit, which is capable of switching the high-frequency current for sealing and the high-frequency current for dissection and outputting the high-frequency currents to the respective electrodes.

The heater driving circuit 41c is a circuit that outputs, to the treatment instrument 2, an electric current for heaters for heating the heaters 24a and 24b in order to seal the biological tissue.

The electric current from the heater driving circuit 41c is supplied to the heaters 24a and 24b. Resistance R of each of the heaters 24a and 24b detected by the detection circuit 42b is monitored by the control section 31. The control section 31 calculates temperatures of each of the heaters 24a and 24b from a resistance value of the resistance R detected by the detection circuit 42b and controls temperatures of the heaters 24a and 24b on the basis of the calculated temperature. The biological tissue is fused at temperature between 150° C. and 200° C. at which decay of protein of the biological tissue does not start.

The heater driving circuit 41c is a circuit driven during a mode M3. The mode M3 is a mode in which sealing treatment with homogeneous fusion of the biological tissue is possible because the biological tissue is heated at high temperature.

The heater driving circuit 41d is a circuit that outputs, to the treatment instrument 2, an electric current for heaters for heating the heater 27 in order to dissect the biological tissue.

The electric current from the heater driving circuit 41d is supplied to the heater 27. The resistance R of the heater 27 detected by the detection circuit 42b is monitored by the control section 31. The control section 31 calculates temperature of the heater 27 from a resistance value of the resistance R detected by the detection circuit 42b and controls the temperature of the heater 27 on the basis of the calculated temperature. The biological tissue is dissected at temperature between 250° C. and 300° C. for facilitating decay of protein of the biological tissue.

The heater driving circuit 41d is a circuit driven during a mode M4.

The temperature of the biological tissue treated by the modes M1 to M4 rises in the order of the mode M1, the mode M3, the mode M4, and the mode M2.

Therefore, the respective electrodes of the holding section 13 are provided in at least one of the jaw members 13a and 13b and configure a high-frequency-energy output section capable of outputting first high-frequency energy in the mode M1 for sealing the biological tissue by setting the biological tissue to a first sealing temperature and second high-frequency energy in the mode M2 for dissecting the biological tissue at a first dissection temperature.

The respective heaters of the holding section 13 are provided at least in one of the jaw members 13a and 13b and configure a thermal-energy output section capable of outputting first thermal energy in the mode M3 for sealing the biological tissue by setting the biological tissue to a second sealing temperature higher than the first sealing temperature and second thermal energy in the mode M4 for dissecting the biological tissue at a second dissection temperature lower than the first dissection temperature.

Note that temperatures of the heaters 24a, 24b, and 27 are calculated on the basis of resistance values of the respective heaters. However, the temperatures of the heaters 24a, 24b, and 27 may be detected by a temperature sensor provided near each of the heaters 24a, 24b, and 27.

Furthermore, the heater driving circuits 41c and 41d are individual circuits. However, the heater driving circuits 41c and 41d may be realized by one circuit, which is capable of switching the electric current for heaters for sealing and the electric current for heaters for dissection and outputting the electric currents to the respective heaters.

As explained above, the main body apparatus 3 has four output modes of the mode M1 serving as a first output mode for a first high-frequency energy output, the mode M2 serving as a second output mode for a second high-frequency energy output, the mode M3 serving as a third output mode for a first thermal energy output, and the mode M4 serving as a fourth output mode for a second thermal energy output.

The control section 31 performs an output of first high-frequency energy on the basis of the mode M1, performs an output of second high-frequency energy on the basis of the mode M2, performs an output of first thermal energy on the basis of the mode M3, and performs an output of second thermal energy on the basis of the mode M4.

The output-sequence setting section 33 is an operation section that sets an output sequence. The output-sequence setting section 33 includes a button group for setting respective output sequences.

Buttons 51, 52, 53, 54, and 55 are respectively buttons for setting the output sequence to output sequences OS1, OS2, OS3, OS4, and OS5 explained below.

The surgeon can designate a desired output sequence by operating a desired button on a front panel of the main body apparatus 3.

The input section 34 is an input device for setting temperature values, voltage values of high-frequency energy outputs, impedance thresholds for a stop of the high-frequency energy outputs, temperatures of the heaters, resistance values for a stop of heating of the heaters, maximum output continuation time periods, and the like in the respective modes included in the respective output sequences. Therefore, the surgeon is capable of setting the first sealing temperature, the second sealing temperature, the first dissection temperature, and the second dissection temperature in the input section 34.

In FIG. 7, the input section 34 is shown as one block. However, up-down keys, numerical value input buttons, and the like are included in the input section 34. The output-sequence setting section 33 and the input section 34 are disposed on the front panel of the main body apparatus 3.

The display section 35 is a display panel such as a liquid crystal display. On the display section 35, various values and the like set for each of the output sequences set in the output-sequence setting section 33 are displayed.

In the storage section 36, order of the respective modes in the respective output sequences, output sequence information such as various thresholds indicating switching timings, and various values set concerning the respective modes are stored.

The speaker 37 outputs alarm sound, output sound during an output, and the like.

The surgeon sets a desired output sequence and steps on the footswitch 4, whereby the treatment instrument 2 performs a high-frequency energy or thermal energy output in the set output sequence.

(Output Sequences)

Output sequences are explained.

A plurality of output sequences can be set in the main body apparatus 3. Each of the output sequences is configured from a plurality of, that is, four output modes. As the output modes, there are the mode M1 for performing a high-frequency energy output for sealing, the mode M2 for performing a high-frequency energy output for dissection, the mode M3 for performing a thermal energy output for sealing, and the mode M4 for performing a thermal energy output for dissection.

In the mode M1, the high-frequency output circuit 41a is driven. In the mode M2, the high-frequency output circuit 41b is driven. In the mode M3, the heater driving circuit 41c is driven. In the mode M4, the heater driving circuit 41d is driven.

The control section 31 of the main body apparatus 3 controls temperature of each of the high-frequency energy output sections and the thermal-energy output sections to output, in the output sequences OS1 to OS4 explained below, second thermal energy in the mode M4 by the respective heaters, which are the thermal-energy output sections, after an output of first high-frequency energy in the mode M1 by the respective electrodes, which are the high-frequency-energy output sections.

The respective output sequences are explained.

1) Output Sequence OS1

Figure 8:
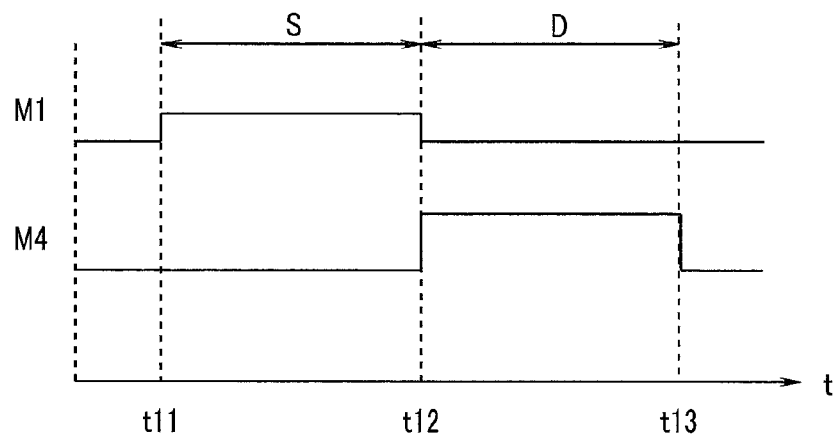
FIG. 8 is a time chart for explaining an output sequence OS1 according to the embodiment of the present invention.

FIG. 8 is a time chart for explaining the output sequence OS1.

The output sequence OS1 is a sequence configured from the modes M1 and M4.

After the surgeon depresses the button 51, as shown in FIG. 8, a sealing phase S by the mode M1 is started from time t11 when the footswitch 4 is stepped on by a foot and turned on. A dissection phase D by the mode M4 is automatically started at time t12 when the mode M1 ends. The control section 31 drives the high-frequency output circuit 41a in the mode M1. The control section 31 drives the heater driving circuit 41d in the mode M4. At time t13, the mode M4 ends.

Therefore, the button 51 configures a first instructing section that instructs execution of the output sequence OS1, which is a first output sequence for changing the output mode of the main body apparatus 3 to the mode M4, which is the fourth output mode, after the mode M1, which is the first output mode.

During the mode M1, the control section 31 monitors an output of the detection circuit 42a and ends the mode M1 when the impedance Z detected by the detection circuit 42a reaches a predetermined threshold ZTH1. Simultaneously with the end of the mode M1, the mode M4 is started. During the mode M4, the control section 31 monitors an output of the detection circuit 42b and automatically ends the mode M4 when a resistance value of the resistance R detected by the detection circuit 42b reaches a predetermined threshold RTH1 or after a set time period TTH1 elapses after the resistance value reaches the threshold RTH1.

The thresholds ZTH1, RTH1, and TTH1 in the output sequence OS1 are set in advance in the input section 34 and stored in the storage section 36. Maximum output continuation time periods of the respective modes in the output sequence OS1 may also be set.

In the output sequence OS1, after the end of the high-frequency energy output in the sealing phase S, temperature of the biological tissue is raised by thermal energy and dissection is performed in the dissection phase D. Therefore, a sealing force of an entire sealed portion of the biological tissue such as a blood vessel is improved and sealing unevenness less easily occurs.

As explained above, in the output sequence OS1, the high-frequency current for sealing is supplied to the electrodes 23a and 23b by the mode M1. The mode M4 is started simultaneously with the end of the mode M1.

Therefore, the output sequence OS1 has an effect that it is possible to improve a sealing property of a severed section such as a blood vessel with thermal energy after quickly raising temperature of a biological tissue in a vicinity to be dissected to high temperature of approximately 100° C.

2) Output Sequence OS2

Figure 9:
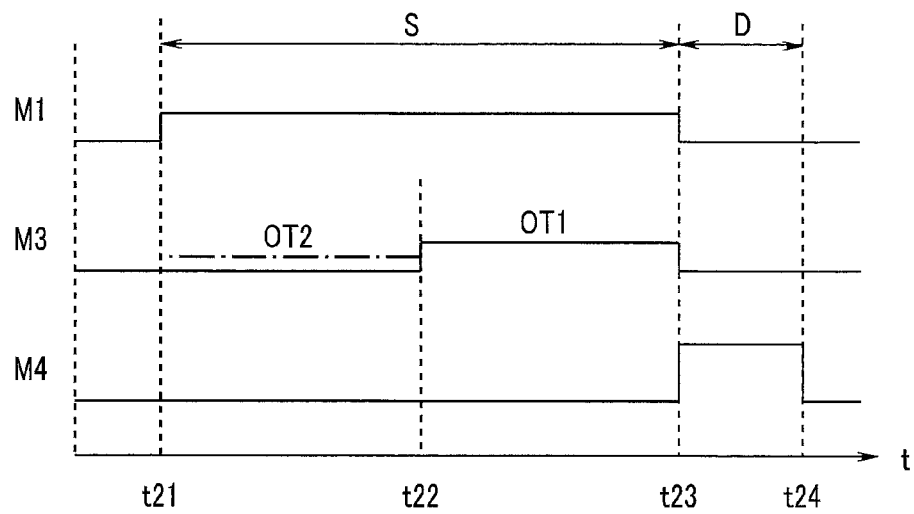
FIG. 9 is a time chart for explaining an output sequence OS2 according to the embodiment of the present invention.

FIG. 9 is a time chart for explaining the output sequence OS2.

The output sequence OS2 is a sequence configured from the modes M1, M3, and M4.

After the surgeon depresses the button 52, as shown in FIG. 9, the sealing phase S by the mode M1 is started from time t21 when the footswitch 4 is stepped on by a foot and turned on. The mode M3 is automatically started halfway in an output in the mode M1. The dissection phase D by the mode M4 is automatically started at time t23 when the modes M1 and M3 end. The mode M4 automatically ends at time t24.

Therefore, the button 52 configures a second instructing section that instructs execution of the output sequence OS2, which is a second output sequence for changing the output mode of the main body apparatus 3 from the mode M1, which is the first output mode, to the mode M4, which is the fourth output mode, through the mode M3, which is the third output mode.

In the output sequence OS2, the mode M3 is started at time t22 when the impedance Z detected by the detection circuit 42a reaches a predetermined threshold ZTH2 while the high-frequency current for sealing is supplied to the electrodes 23a and 23b by the mode M1. That is, when the impedance Z between the jaw members 13a and 13b, which are the pair of holding members, in the mode M1, which is the first output mode, reaches the predetermined threshold ZTH2, the control section 31 starts the mode M3, which is the third output mode.

When the impedance Z detected by the detection circuit 42a reaches a predetermined threshold ZTH3 or after a predetermined time period TTH2 elapses, the control section 31 ends the modes M1 and M3. Simultaneously with the end of the modes M1 and M3, the mode M4 is started. The control section 31 monitors an output of the detection circuit 42b and ends the mode M4 when a resistance value of the resistance R detected by the detection circuit 42b reaches a predetermined threshold RTH2.

The thresholds ZTH2, ZTH3, RTH2, and TTH2 in the output sequence OS1 are set in advance in the input section 34 and stored in the storage section 36. Maximum output continuation time periods of the respective modes in the output sequence OS2 may also be set.

In the output sequence OS2, temperature of the biological tissue is raised by thermal energy and dissection is performed from the start of the sealing phase S to the dissection phase D. Therefore, a sealing force of an entire sealed portion of the biological tissue such as a blood vessel is improved and sealing unevenness less easily occurs.

As explained above, in the output sequence OS2, the control section 31 starts the mode M3 halfway in the mode M1 and, while improving the sealing property of a severed portion by raising the temperature of the biological tissue to high temperature at which the biological tissue is not dissected, thereafter starts the mode M4 for raising the temperature of the biological tissue to temperature at which dissection is possible. Therefore, it is possible to quickly perform the severing while improving the sealing property of a severed section such as a blood vessel with thermal energy.

Note that, as a modified example of the output sequence OS2, the mode M4 may be started from time before the end time t23 of the mode M1.

Figure 10:
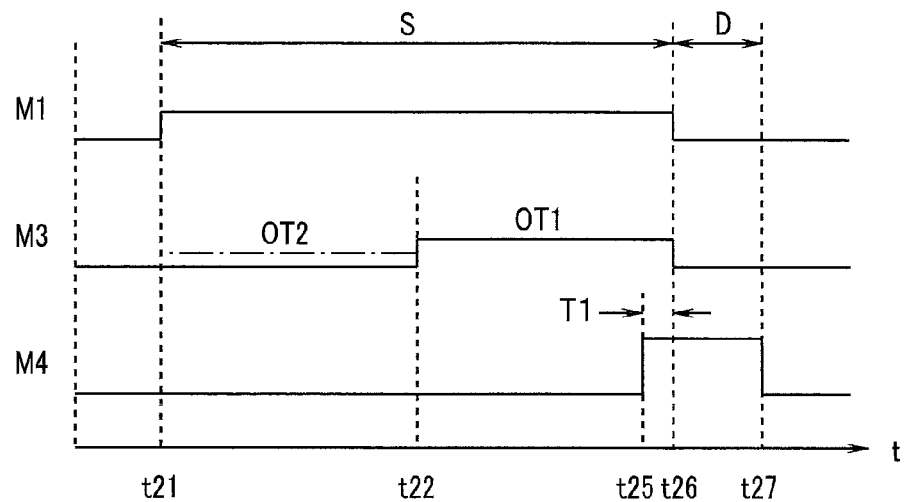
FIG. 10 is a time chart for explaining a modified example OS2-1 of the output sequence OS2 according to the embodiment of the present invention.

FIG. 10 is a time chart for explaining a modified example OS2-1 of the output sequence OS2. In the modified example OS2-1 of the output sequence OS2, during the output in the mode M3, the control section 31 predicts time when the impedance Z detected by the detection circuit 42a reaches the predetermined threshold ZTH3 and starts the mode M4 from a predetermined time period T1, for example, 0.5 second before the predicted time. That is, execution of the mode M4, which is the fourth output mode, is started before an end of the mode M3, which is the third output mode.

Therefore, the predetermined time period T1 in the modified example OS2-1 of the output sequence OS2 is also set in advance and stored in the storage section 36.

In the modified example OS2-1, compared with the output sequence OS2, it is possible to achieve a reduction in an overall time period of the output sequence.

Note that, in the case of the modified example, the modes M1, M3, and M4 are in a simultaneous output state for the predetermined time period T1. However, the outputs in the modes M1 and M4 may be reduced for the predetermined time period T1.

Before the predetermined time period T1 starts, if electric power during the outputs in the modes M1 and M3 is represented as P1, output levels in the modes M1 and M3 may be reduced such that electric power P2 during the outputs in the modes M1, M3, and M4 for the predetermined time period T1 is the same as P1.

In this way, the electric power P2 during the outputs in the modes M1, M3, and M4 for the predetermined time period T1 is set the same as P1. Consequently, it is possible to reduce a power supply capacity of the main body apparatus 3.

Furthermore, in the output sequence OS2 and the modified example OS2-1 of the output sequence OS2 explained above, the mode M3 starts halfway in the output of the mode M1. However, the control section 31 may control the heater driving circuit 41c to start the mode M3 at temperature OT2 lower than predetermined temperature OT1 simultaneously with the start of the output in the mode M1 and raise the temperature OT2 to the predetermined temperature OT1 halfway.

As indicated by an alternate long and short dash line in FIG. 9 and FIG. 10, simultaneously with the start of the mode M1, heating of the biological tissue is performed at the temperature OT2 by the mode M3 and, after time t22, the heating of the biological tissue is performed such that the temperature OT2 rises to the predetermined temperature OT1.

3) Output Sequence OS3

Figure 11:
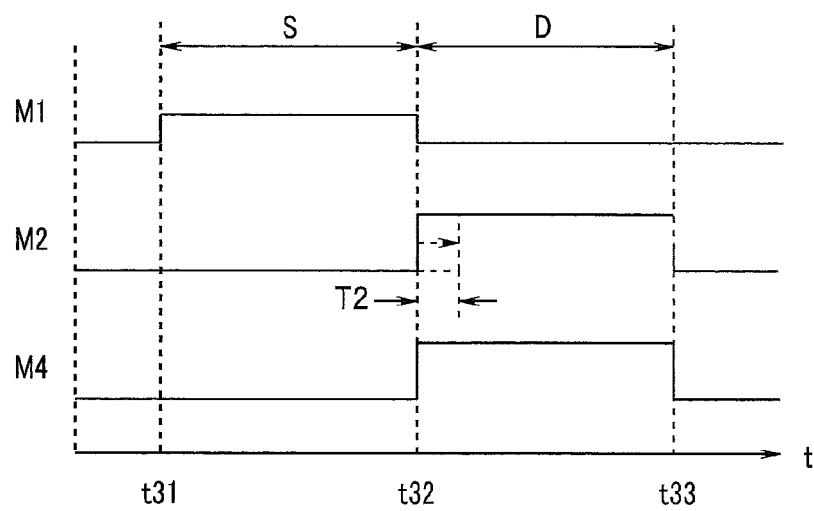
FIG. 11 is a time chart for explaining an output sequence OS3 according to the embodiment of the present invention.

FIG. 11 is a time chart for explaining the output sequence OS3.

The output sequence OS3 is a sequence configured from the modes M1, M2, and M4.

After the surgeon depresses the button 53, as shown in FIG. 11, the sealing phase S by the mode M1 is started from time t31 when the footswitch 4 is stepped on by a foot and turned on. At time t32 when the mode M1 ends, the dissection phase D by the modes M2 and M4 is automatically started. At time t33, the modes M2 and M4 automatically end.

Therefore, the button 53 configures a third instructing section that instructs execution of the output sequence OS3, which is a third output sequence for changing the output mode of the main body apparatus 3 from the mode M1, which is the first output mode, to the mode M2, which is the second output mode, together with the mode M4, which is the fourth output mode.

In the output sequence OS3, when the impedance Z detected by the detection circuit 42a reaches a predetermined threshold ZTH4 when the high-frequency current for sealing is supplied to the electrodes 23a and 23b by the mode M1, the control section 31 starts an operation based on the modes M2 and M4. When the impedance Z detected by the detection circuit 42a reaches a predetermined threshold ZTH5 or after a predetermined time period TTH3 elapses, the control section 31 ends the operation in the modes M2 and M4.

Note that the modes M2 and M4 may end when a resistance value of the resistance R detected by the detection circuit 42b reaches a predetermined threshold RTH3. That is, the control section 31 may instruct execution of the mode M2, which is the second output mode, after changing the output mode of the main body apparatus 3 from the mode M1, which is the first output mode, to the mode M4, which is the fourth output mode.

The threshold ZTH4, ZTH5 (or RTH3), or TTH3 in the output sequence OS3 is set in advance in the input section 34 and stored in the storage section 36. Maximum output continuation times of the respective modes in the output sequence OS3 may also be set.

In the output sequence OS3, after the end of the sealing phase S, in the dissection phase D, temperature of the biological tissue is raised with thermal energy and dissection is performed. Therefore, a sealing force of an entire sealed portion of the biological tissue such as a blood vessel is improved and sealing unevenness less easily occurs.

When dissection of the biological tissue is performed only in the mode M2, an electric discharge state changes according to an ambient temperature and the like. However, in the output sequence OS3, the mode M2 for raising the temperature of the biological tissue to temperature at which dissection is possible operates together with the mode M4. As a result, electric discharge by the mode M2 is performed in a state in which the biological tissue is heated by the mode M4. Therefore, an electric discharge amount does not decrease. It is possible to quickly perform the severing while improving a sealing property of a severed section with less electric power.

In particular, in the output sequence OS3, since an operation based on the mode M2 simultaneously with the mode M4 is executed, it is possible to continue to give heat to tissues such as a ligament and a bronchus where it is difficult to cause electric discharge. Therefore, quality of dissection is improved.

Since an electrode 28, which is an electrode for dissection, is also heated, there is also an effect that a dark current before occurrence of electric discharge is increased to easily cause electric discharge.

Note that, as indicated by a dotted line in FIG. 11, rather than simultaneously starting the modes M4 and M2, the control section 31 may delay start time of the mode M2 by a predetermined time period T2 from the start of the mode M4.

In the mode M4, the temperature of the biological tissue is 250° C. to 300° C. In the mode M2, the temperature of the biological tissue is 300° C. to 400° C. Therefore, it is possible to efficiently and quickly perform the dissection by starting the operation based on the mode M4 before the start of the mode M2.

Therefore, when changing the output mode of the main body apparatus 3 from the mode M1, which is the first output mode, to the mode M2, which is the second output mode, together with the mode M4, which is the fourth output mode, the control section 31 may start the mode M2 later than the start of the mode M4.

4) Output Sequence OS4

Figure 12:
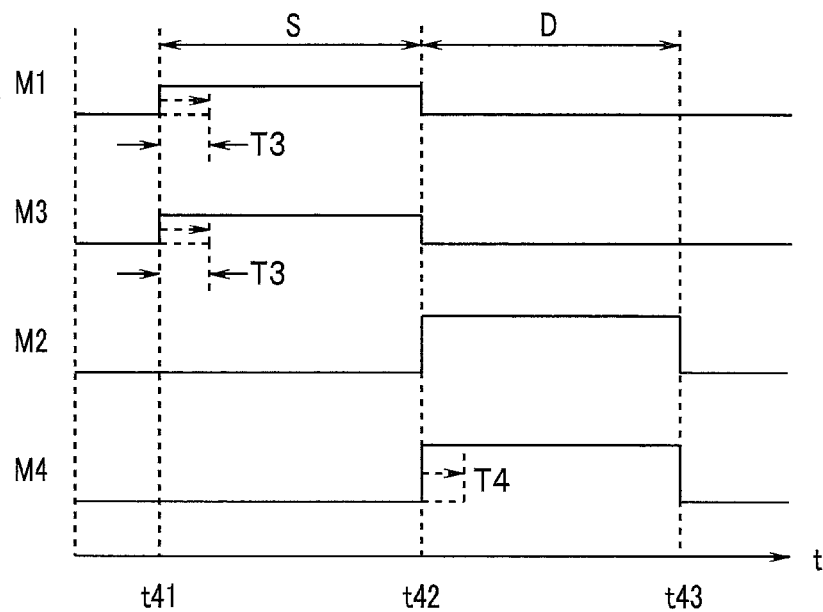
FIG. 12 is a time chart for explaining an output sequence OS4 according to the embodiment of the present invention.

FIG. 12 is a time chart for explaining the output sequence OS4.

The output sequence OS4 is a sequence configured from the modes M1, M2, M3, and M4.

After the surgeon depresses the button 54, as shown in FIG. 12, the sealing phase S by the modes M1 and M3 is started from time t41 when the footswitch 4 is stepped on by a foot and turned on. At time t42 when the modes M1 and M3 end, the dissection phase D by the modes M2 and M4 is automatically started. At time t43, the modes M2 and M4 automatically end.

Therefore, the button 54 configures a fourth instructing section that instructs the mode M3 to be executed together with the mode M1 and the mode M2 to be executed together with the mode M4 when the output mode of the main body apparatus 3 is changed from the mode M1, which is the first output mode, to the mode M4, which is the fourth output mode.

The control section 31 monitors an output of the detection circuit 42a while the high-frequency current for sealing is supplied to the electrodes 23a and 23b by the mode M1 and heating for sealing is performed by the mode M3. When the impedance Z detected by the detection circuit 42a reaches a predetermined threshold ZTH6 or after a predetermined time period TTH4 elapses, the control section 31 ends an operation based on the modes M1 and M3. Simultaneously with the end of the modes M1 and M3, the control section 31 starts an operation based on the modes M2 and M4. When the impedance Z detected by the detection circuit 42a reaches a predetermined threshold ZTH7 or after a predetermined time TTH5 elapses, the control section 31 ends the operation based on the modes M2 and M4.

Note that the modes M1 and M3 may end when a resistance value of the resistance R detected by the detection circuit 42b reaches a predetermined threshold RTH4 or after a predetermined time period TTH6 elapses.

Similarly, the modes M2 and M4 may end when a resistance value of the resistance R detected by the detection circuit 42b reaches a predetermined threshold RTH5 or after a predetermined time period TTH7 elapses.

The threshold ZTH6 (or RTH4), ZTH7 (or RTH5), or TTH6 or TTH7 in the output sequence OS3 is set in advance in the input section 34 and stored in the storage section 36.

Note that, as indicated by a dotted line in FIG. 12, rather than simultaneously starting the modes M1 and M3, the control section 31 may delay start time of one of the mode M1 and the mode M3 by a predetermined time period T3 from start time of the other.

That is, the control section 31 may start the mode M1, which is the first output mode, later than the mode M3, which is the third output mode, by the predetermined time period T3 or may start the mode M3 later than the start of the mode M1 by the predetermined time period T3.

Similarly, rather than simultaneously starting the modes M2 and M4, the control section 31 may delay start time of one of the mode M2 and the mode M4 by a predetermined time period T4 from start time of the other. That is, the control section 31 may start the mode M4, which is the fourth output mode, later than the mode M2, which is the second output mode.

In particular, by starting the mode M2 earlier than the mode M4, it is possible to reduce a dissection time period. Further, in the case of a biological tissue, a biological tissue less easily dissected only by high-frequency energy for dissection sometimes remains. It is possible to facilitate dissection of such a biological tissue by adding the mode M2.

In the output sequence OS4, the dissection is performed such that the temperature of the biological tissue rises from the sealing phase S to the dissection phase D. Therefore, a sealing force of an entire sealed portion of the biological tissue is improved and sealing unevenness less easily occurs.

As explained above, the mode M2 for raising the temperature of the biological tissue to the temperature at which dissection is possible is started together with the mode M4. Therefore, it is possible to quickly perform the severing while improving a sealing property of a severed section such as a blood vessel with the thermal energy.

In particular, as in the output sequence OS3, in the output sequence OS4, since the mode M2 is executed simultaneously with the mode M4, the control section 31 can continue to give heat to tissues such as a ligament and a bronchus where it is difficult to cause electric discharge. Therefore, quality of dissection is improved.

Since the electrode 28, which is the electrode for dissection, is also heated, there is also an effect that a dark current before occurrence of electric discharge is increased to easily cause the electric discharge.

Further, with the output sequence OS4, there is an effect that, since the mode M3 is also outputted simultaneously with the mode M1, it is also possible to improve quality of sealing and, since the mode M4 is also outputted simultaneously with the mode M2, it is possible to quickly perform dissection of the biological tissue.

Note that, in the output sequence OS4 as well, when the mode M1 and the mode M3 are simultaneously operating and when the mode M2 and the mode M4 are simultaneously operating, as indicated by an alternate long and short dash line in FIG. 9 and FIG. 10, an output level of one of the two modes may be reduced during a start of the operation and increased halfway.

5) Output Sequence OS5

Figure 13:
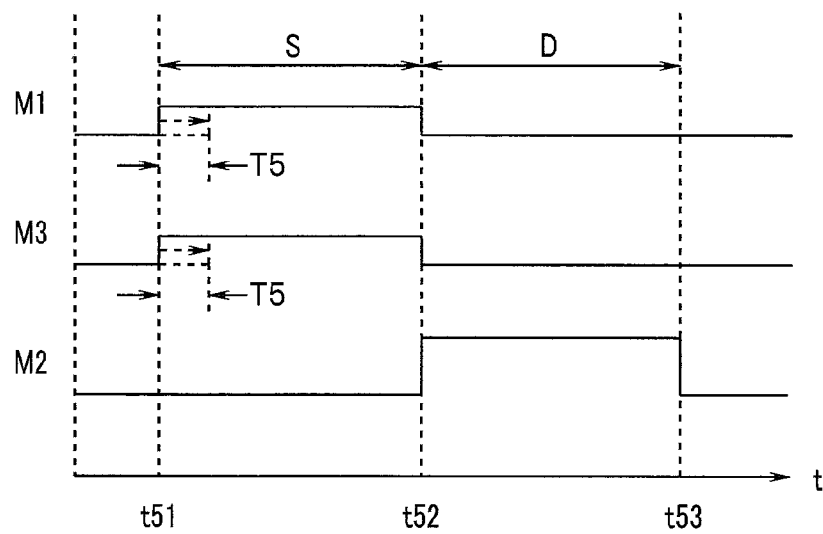
FIG. 13 is a time chart for explaining an output sequence OS5 according to the embodiment of the present invention.

FIG. 13 is a time chart for explaining the output sequence OS5.

The output sequence OS5 is a sequence configured from the modes M1, M2, and M3.

After the surgeon depresses the button 51, as shown in FIG. 13, the sealing phase S by the modes M1 and M3 is started from time t51 when the footswitch 4 stepped on by a foot and turned on. At time t52 when the modes M1 and M3 end, the dissection phase D by the mode M2 is automatically started. At time t53, the mode M2 automatically ends.

In the output sequence OS5, the mode M1 and the mode M3 are simultaneously started in the sealing phase S. Temperature of a biological tissue to be dissected rises to temperature of 100° C. or more. Therefore, sealing performance is improved.

Note that, as indicated by a dotted line in FIG. 13, rather than simultaneously starting the modes M1 and M3, the control section 31 may delay start time of one of the mode M1 and the mode M3 by a predetermined time period T5 from start time of the other.

Furthermore, in the output sequence OS5 as well, when the mode M1 and the mode M3 are simultaneously operating, as indicated by an alternate long and short dash line in FIG. 9 and FIG. 10, an output may be reduced during a start of the operation of one of the two modes and increased halfway.

As explained above, the main body apparatus 3 includes the five output sequences. The surgeon can select and set an optimum output sequence out of the five output sequences according to a treatment target and perform dissection of a biological tissue with high-frequency energy and thermal energy.

Figure 14:
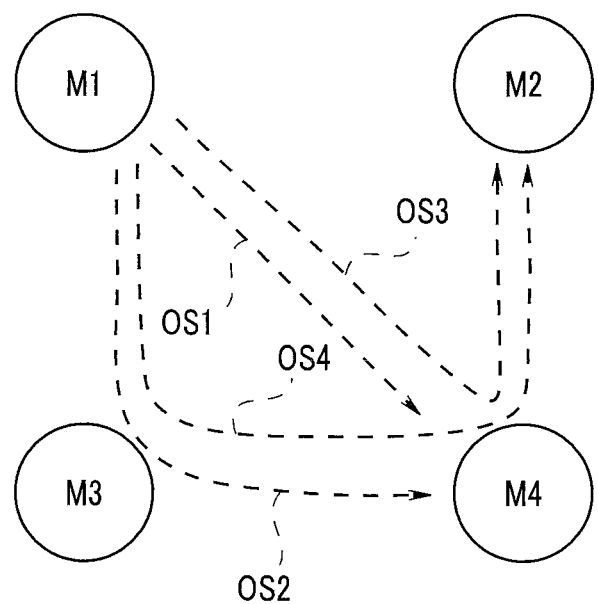
FIG. 14 is a transition chart for explaining a mode transition in the output sequences OS1 to OS4 according to the embodiment of the present invention.

FIG. 14 is a transition chart for explaining a mode transition in the output sequences OS1 to OS4.

As shown in FIG. 14, the output sequence OS1 is a sequence for transitioning from the mode M1 to the mode M4.

The output sequence O52 is a sequence for transitioning from the mode M1 to the mode M4 through the mode M3.

The output sequence O53 is a sequence for transitioning from the mode M1 to the mode M2 through the mode M4 or transitioning from the mode M1 to the modes M4 and M2.

The output sequence OS4 is a sequence for starting an operation based on the mode M3 together with the mode M1 and starting an operation based on the mode M4 together with the mode M2 when transitioning from the mode M1 to the mode M4.

Although not shown in FIG. 14, the output sequence OS5 is a sequence for transitioning from the mode M1 to the mode M4 through the mode M3.

When performing dissection of a biological tissue according to the output sequences, the surgeon can select and set an optimum output sequence according to a treatment target or according to a state of the treatment target and perform the dissection.

Note that, in the embodiment explained above, in the respective modes, a high-frequency energy output and a thermal energy output are fixed. However, for example, as shown in FIG. 15, at least one of the high-frequency energy output and the thermal energy output may be changed stepwise or continuously.

Figure 15:
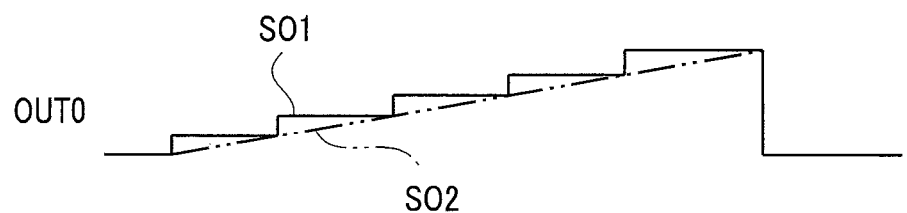
FIG. 15 is a diagram showing a change in an output OUT0 (a high-frequency energy output or a thermal energy output) in respective modes according to the embodiment of the present invention.

FIG. 15 is a diagram showing a change in an output OUT0 (the high-frequency energy output or the thermal energy output) in the respective modes. By changing the high-frequency energy output or the thermal energy output stepwise as indicated by a solid line SO1 or by changing the high-frequency energy output or the thermal energy output continuously as indicated by an alternate long and two short dashes line SO2, it is possible to supply energy matching respective biological tissues to the respective biological tissues and more appropriately perform sealing or dissection.

Furthermore, in the embodiment explained above, in the respective modes, the high-frequency energy output and the thermal energy output are fixed. However, for example, as shown in FIG. 16, at least one of the high-frequency energy output and the thermal energy output may be output discontinuously.

Figure 16:
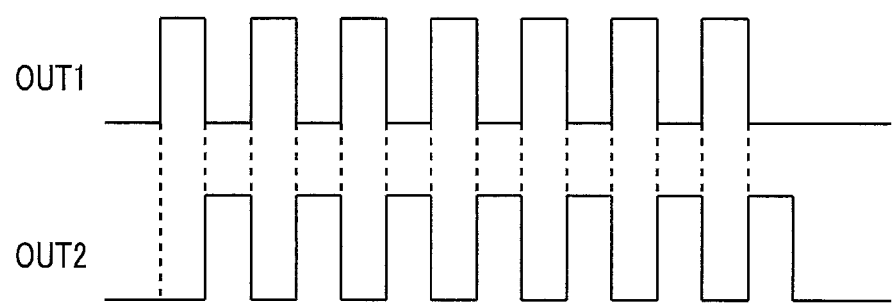
FIG. 16 is a diagram showing changes in outputs in the respective modes, a high-frequency energy output OUT1 and a thermal energy output OUT2, according to the embodiment of the present invention.

FIG. 16 is a diagram showing changes in outputs in the respective modes, a high-frequency energy output OUT1 and a thermal energy output OUT2. By performing the high-frequency energy output or the thermal energy output discontinuously, it is possible to supply energy matching respective biological tissues to the respective biological tissues and more appropriately perform sealing or dissection.

In particular, as shown in FIG. 16, when the outputs in the two modes are simultaneously performed, the outputs in the two modes are performed such that the thermal energy output stops when high-frequency energy is outputted and the high-frequency energy output stops when thermal energy is outputted. When the control section 31 performs such output control, since the high-frequency energy output and the thermal energy output are not simultaneously performed, it is possible to reduce a capacity of a power supply.

Note that the therapeutic treatment apparatus in the embodiment explained above is not only effective for relatively thin lumen organs such as a blood vessel and a lymphatic vessel but also applicable to treatment for thick lumen organs such as a large intestine and a small intestine and solid organs such as a liver. The therapeutic treatment apparatus in the embodiment explained above can perform hemostatic treatment and dissection treatment on the liver and the like.

As explained above, according to the embodiment, when dissection is performed on various biological tissues, it is possible to realize a therapeutic treatment system and an operation method for the therapeutic treatment system that can easily realize dissection treatment with which a dissected biological tissue has a higher sealing ability.

In particular, in the therapeutic treatment system in the embodiment explained above, by performing appropriate setting according to a type of a biological tissue and setting an output sequence, simply by selecting an output sequence corresponding to a biological tissue, the surgeon is capable of easily performing dissection treatment with which a treated biological tissue has a high sealing ability.

The present invention is not limited to the embodiment explained above. Various changes, alterations, and the like are possible within a range in which the gist of the present invention is not changed.

What is claimed is:

1. A therapeutic treatment system for use with a biological tissue that is a treatment target, the therapeutic treatment system comprising:
    a pair of holding members configured to hold the biological tissue such that at least one holding member moves to open and close relatively to the other holding member;
    a high-frequency-energy output section provided in at least one of the holding members and being capable of outputting: (i) first high-frequency energy to seal the biological tissue by setting the biological tissue to a first sealing temperature, and (ii) second high-frequency energy to dissect the biological tissue at a first dissection temperature higher than the first sealing temperature;
    a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature; and
    a processor programmed to:
        control respective temperatures of the high-frequency-energy output section and the thermal-energy output section to output the second thermal energy that dissects the biological tissue by the thermal-energy output section after the output of the first high-frequency energy that seals the biological tissue by the high-frequency-energy output section, wherein:
    the therapeutic treatment system includes, as output modes of the therapeutic treatment system, four output modes of a first output mode for an output of the first high-frequency energy, a second output mode for an output of the second high-frequency energy, a third output mode for an output of the first thermal energy, and a fourth output mode for an output of the second thermal energy, the therapeutic treatment system further includes an instructing section configured to instruct execution of a second output sequence for changing output modes of the therapeutic treatment system from the first output mode to the fourth output mode through the third output mode, the processor is further programmed to:
   output the first high-frequency energy on the basis of the first output mode,
   output the second high-frequency energy on the basis of the second output mode,
   output the first thermal energy on the basis of the third output mode, and
   output the second thermal energy on the basis of the fourth output mode, and the processor is configured to start execution of the fourth output mode before an end of the third output mode.

2. A therapeutic treatment system for use with a biological tissue that is a treatment target, the therapeutic treatment system comprising:
   a pair of holding members configured to hold the biological tissue such that at least one holding member moves to open and close relatively to the other holding member;
   a high-frequency-energy output section provided in at least one of the holding members and being capable of outputting: (i) first high-frequency energy to seal the biological tissue by setting the biological tissue to a first sealing temperature, and (ii) second high-frequency energy to dissect the biological tissue at a first dissection temperature higher than the first sealing temperature;
   a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature; and
   a processor programmed to:
      control respective temperatures of the high-frequency-energy output section and the thermal-energy output section to output the second thermal energy that dissects the biological tissue by the thermal-energy output section after the output of the first high-frequency energy that seals the biological tissue by the high-frequency-energy output section, wherein:
   the therapeutic treatment system includes, as output modes of the therapeutic treatment system, four output modes of a first output mode for an output of the first high-frequency energy, a second output mode for an output of the second high-frequency energy, a third output mode for an output of the first thermal energy, and a fourth output mode for an output of the second thermal energy,
   the therapeutic treatment system further includes an instructing section configured to instruct execution of a second output sequence for changing output modes of the therapeutic treatment system from the first output mode to the fourth output mode through the third output mode, the processor is further programmed to:
   output the first high-frequency energy on the basis of the first output mode,
   output the second high-frequency energy on the basis of the second output mode,
   output the first thermal energy on the basis of the third output mode, and
   output the second thermal energy on the basis of the fourth output mode, and the processor is configured to start execution of the third output mode when impedance between the pair of holding members in the first output mode reaches a predetermined threshold or when a predetermined time period elapses.

3. A therapeutic treatment system for use with a biological tissue that is a treatment target, the therapeutic treatment system comprising:
   a pair of holding members configured to hold the biological tissue such that at least one holding member moves to open and close relatively to the other holding member;
   a high-frequency-energy output section provided in at least one of the holding members and being capable of outputting: (i) first high-frequency energy to seal the biological tissue by setting the biological tissue to a first sealing temperature, and (ii) second high-frequency energy to dissect the biological tissue at a first dissection temperature higher than the first sealing temperature;
   a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature; and
   a processor programmed to:
      control respective temperatures of the high-frequency-energy output section and the thermal-energy output section to output the second thermal energy that dissects the biological tissue by the thermal-energy output section after the output of the first high-frequency energy that seals the biological tissue by the high-frequency-energy output section, wherein:
   the therapeutic treatment system includes, as output modes of the therapeutic treatment system, four output modes of a first output mode for an output of the first high-frequency energy, a second output mode for an output of the second high-frequency energy, a third output mode for an output of the first thermal energy, and a fourth output mode for an output of the second thermal energy,
   the processor is further programmed to:
      output the first high-frequency energy on the basis of the first output mode,
      output the second high-frequency energy on the basis of the second output mode,
      output the first thermal energy on the basis of the third output mode, and
      output the second thermal energy on the basis of the fourth output mode, and
   the therapeutic treatment system includes an instructing section configured to instruct execution of the second output mode after changing output modes of the therapeutic treatment system from the first output mode to the fourth output mode or instruct execution of a third output sequence for changing output modes of the therapeutic treatment system from the first output mode to the second output mode together with the fourth output mode.

4. The therapeutic treatment system according to claim 3, wherein, when output modes of the therapeutic treatment system are changed from the first output mode to the second output mode together with the fourth output mode, the second output mode is started later than a start of the fourth output mode.

5. A therapeutic treatment system for use with a biological tissue that is a treatment target, the therapeutic treatment system comprising:
  a pair of holding members configured to hold the biological tissue such that at least one holding member moves to open and close relatively to the other holding member;
  a high-frequency-energy output section provided in at least one of the holding members and being capable of outputting: (i) first high-frequency energy to seal the biological tissue by setting the biological tissue to a first sealing temperature, and (ii) second high-frequency energy to dissect the biological tissue at a first dissection temperature higher than the first sealing temperature;
  a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature; and
  a processor programmed to:
    control respective temperatures of the high-frequency-energy output section and the thermal-energy output section to output the second thermal energy that dissects the biological tissue by the thermal-energy output section after the output of the first high-frequency energy that seals the biological tissue by the high-frequency-energy output section, wherein:
  the therapeutic treatment system includes, as output modes of the therapeutic treatment system, four output modes of a first output mode for an output of the first high-frequency energy, a second output mode for an output of the second high-frequency energy, a third output mode for an output of the first thermal energy, and a fourth output mode for an output of the second thermal energy,
  the processor is further programmed to:
    output the first high-frequency energy on the basis of the first output mode,
    output the second high-frequency energy on the basis of the second output mode,
    output the first thermal energy on the basis of the third output mode, and
    output the second thermal energy on the basis of the fourth output mode, and
  the therapeutic treatment system includes an instructing section configured to instruct, when output modes of the therapeutic treatment system are changed from the first output mode to the fourth output mode, the third output mode to be executed together with the first output mode and the second output mode to be executed together with the fourth output mode.

6. The therapeutic treatment system according to claim 5, wherein the first output mode is started later than a start of the third output mode.

7. The therapeutic treatment system according to claim 5, wherein the third output mode is started later than a start of the first output mode.

8. The therapeutic treatment system according to claim 5, wherein the fourth output mode is started later than a start of the second output mode.

9. The therapeutic treatment system according to claim 1, wherein the first sealing temperature is a temperature between 60° C. and 100° C.

10. The therapeutic treatment system according to claim 1, wherein the first dissection temperature is a temperature between 200° C. and 400° C.

11. The therapeutic treatment system according to claim 1, wherein the second sealing temperature is a temperature between 150° C. and 200° C.

12. The therapeutic treatment system according to claim 1, wherein the second dissection temperature is a temperature between 250° C. and 300° C.

13. The therapeutic treatment system according to claim 1, wherein the first sealing temperature, the second sealing temperature, the first dissection temperature, and the second dissection temperature can be set.

14. An operation method for use with a biological tissue that is a treatment target, and a therapeutic treatment system including a pair of holding members configured to hold the biological tissue, such that at least one holding member moves to open and close relatively to the other holding member, a high-frequency-energy output section provided in at least one of the grasping members and being capable of: (i) outputting first high-frequency energy to seal the biological tissue by setting the biological tissue to a first sealing temperature, and (ii) second high-frequency energy to dissect the biological tissue at a first dissection temperature higher than the first sealing temperature, a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature, and a processor, the method comprising:
  controlling, by the processor, the high-frequency-energy output section and the thermal-energy output section to output the second thermal energy that dissects the biological tissue by the thermal-energy output section after the output of the first high-frequency energy that seals the biological tissue by the high-frequency-energy output section, wherein:
  the therapeutic treatment system includes, as output modes, four output modes of a first output mode for an output of the first high-frequency energy, a second output mode for an output of the second high-frequency energy, a third output mode for an output of the first thermal energy, and a fourth output mode for an output of the second thermal energy, and
  the method further comprises:
    outputting, by the processor, the first high-frequency energy on the basis of the first output mode,
    outputting, by the processor, the second high-frequency energy on the basis of the second output mode,
    outputting, by the processor, the first thermal energy on the basis of the third output mode, outputting, by the processor, the second thermal energy on the basis of the fourth output mode, and the second output mode is executed after: changing output modes of the therapeutic treatment system from the first output mode to the fourth output mode, or changing output modes of the therapeutic treatment system from the first output mode to the second output mode together with the fourth output mode.

15. An operation method for use with a biological tissue that is a treatment target, and a therapeutic treatment system including a pair of holding members configured to hold the biological tissue, such that at least one holding member moves to open and close relatively to the other holding member, a high-frequency-energy output section provided in at least one of the grasping members and being capable of: (i) outputting first high-frequency energy to seal the biological tissue by setting the biological tissue to a first sealing temperature, and (ii) second high-frequency energy to dissect the biological tissue at a first dissection temperature higher than the first sealing temperature, a thermal-energy output section provided in at least one of the holding members and being capable of outputting: (A) first thermal energy to seal the biological tissue by setting the biological tissue to a second sealing temperature higher than the first sealing temperature, and (B) second thermal energy to dissect the biological tissue at a second dissection temperature lower than the first dissection temperature and higher than the second sealing temperature, and a processor, the method comprising:

controlling, by the processor, the high-frequency-energy output section and the thermal-energy output section to output the second thermal energy that dissects the biological tissue by the thermal-energy output section after the output of the first high-frequency energy that seals the biological tissue by the high-frequency-energy output section, wherein:

the therapeutic treatment system includes, as output modes, four output modes of a first output mode for an output of the first high-frequency energy, a second output mode for an output of the second high-frequency energy, a third output mode for an output of the first thermal energy, and a fourth output mode for an output of the second thermal energy, and the method further comprises:
outputting, by the processor, the first high-frequency energy on the basis of the first output mode,
outputting, by the processor, the second high-frequency energy on the basis of the second output mode,
outputting, by the processor, the first thermal energy on the basis of the third output mode,
outputting, by the processor, the second thermal energy on the basis of the fourth output mode, and
when output modes of the therapeutic treatment system are changed from the first output mode to the fourth output mode, the third output mode is executed together with the first output mode and the second output mode is executed together with the fourth output mode.

* * * * *